United States Patent
Freeman et al.

(10) Patent No.: US 10,145,811 B2
(45) Date of Patent: Dec. 4, 2018

(54) RADIO FREQUENCY IDENTIFICATION MONITORING OF STENTS

(71) Applicant: Abbott Cardiovascular Systems Inc., Santa Clara, CA (US)

(72) Inventors: Abigail Freeman, Del Mar, CA (US); David C. Gale, Kennesaw, GA (US); Bin Huang, Pleasanton, CA (US); Daniel Castro, Mountain View, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 15/695,776

(22) Filed: Sep. 5, 2017

(65) Prior Publication Data

US 2017/0363554 A1  Dec. 21, 2017

Related U.S. Application Data

(60) Division of application No. 14/609,184, filed on Jan. 29, 2015, now Pat. No. 9,772,299, which is a
(Continued)

(51) Int. Cl.
| | |
|---|---|
| *G01N 25/00* | (2006.01) |
| *G01N 25/72* | (2006.01) |
| *A61L 2/08* | (2006.01) |
| *A61L 2/10* | (2006.01) |
| *A61F 2/82* | (2013.01) |
| *A61B 90/90* | (2016.01) |

(Continued)

(52) U.S. Cl.
CPC ............. *G01N 25/72* (2013.01); *A61B 90/90* (2016.02); *A61B 90/98* (2016.02); *A61F 2/82* (2013.01); *A61L 2/081* (2013.01); *A61L 2/082* (2013.01); *A61L 2/085* (2013.01); *A61L 2/087* (2013.01); *A61L 2/10* (2013.01); *A61F 2/06* (2013.01); *A61F 2250/0085* (2013.01); *A61L 2202/14* (2013.01)

(58) Field of Classification Search
None
See application file for complete search history.

(56) References Cited

U.S. PATENT DOCUMENTS

| 3,687,135 A | 8/1972 | Stroganov et al. |
|---|---|---|
| 3,839,743 A | 10/1974 | Schwarcz |

(Continued)

FOREIGN PATENT DOCUMENTS

| CA | 2 472 809 | 12/2005 |
|---|---|---|
| DE | 44 07 079 | 9/1994 |

(Continued)

OTHER PUBLICATIONS

"Free2move active RFIDs system", Free2move AB, downloaded from: http://web.archive.org/web/20060209061857/http://www.free2move.se/prod_rfid.shtml, 1 pg, (2004).

(Continued)

*Primary Examiner* — Paul M. West
*Assistant Examiner* — Mark A Shabman
(74) *Attorney, Agent, or Firm* — Squire Patton Boggs (US) LLP

(57) ABSTRACT

A method and system of monitoring environmental exposure of stents using radiofrequency identification is disclosed.

15 Claims, 1 Drawing Sheet

Related U.S. Application Data continuation of application No. 12/796,546, filed on Jun. 8, 2010, now Pat. No. 9,188,558, which is a division of application No. 11/486,688, filed on Jul. 13, 2006, now Pat. No. 7,757,543.

(51) Int. Cl.
*A61B 90/98* (2016.01)
*A61F 2/06* (2013.01)

(56) References Cited

U.S. PATENT DOCUMENTS

| | | |
|---|---|---|
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |

(56) References Cited

U.S. PATENT DOCUMENTS

| | | |
|---|---|---|
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,405,863 B1 * | 6/2002 | Dhindsa ............... B65D 1/36 206/370 |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Went et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,575,716 B2 * | 8/2009 | Wu ............... A61L 2/20 422/292 |
| 7,602,284 B2 * | 10/2009 | Wong ............... A61L 2/186 340/539.22 |
| 7,639,136 B1 * | 12/2009 | Wass ............... G06Q 10/08 340/572.1 |
| 7,757,543 B2 * | 7/2010 | Freeman ............... A61L 2/081 73/25.01 |
| 8,309,022 B2 * | 11/2012 | Huang ............... A61L 2/081 422/1 |

(56) References Cited

U.S. PATENT DOCUMENTS

| | | | |
|---|---|---|---|
| 8,600,374 B1* | 12/2013 | Hertlein | H04M 1/18 |
| | | | 455/425 |
| 9,188,558 B2 | 11/2015 | Freeman et al. | |
| 9,772,299 B2 | 9/2017 | Freeman et al. | |
| 2001/0044652 A1 | 11/2001 | Moore | |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0062148 A1 | 5/2002 | Hart | |
| 2002/0065553 A1 | 5/2002 | Weber | |
| 2002/0111590 A1 | 8/2002 | Davila et al. | |
| 2002/0116050 A1 | 8/2002 | Kocur | |
| 2002/0138133 A1 | 9/2002 | Lenz et al. | |
| 2002/0161114 A1 | 10/2002 | Gunatillake et al. | |
| 2002/0161425 A1* | 10/2002 | Hemerick | A61F 2/95 |
| | | | 623/1.11 |
| 2003/0033001 A1 | 2/2003 | Igaki | |
| 2003/0040790 A1* | 2/2003 | Furst | A61F 2/91 |
| | | | 623/1.11 |
| 2003/0093107 A1 | 5/2003 | Parsonage et al. | |
| 2003/0100865 A1 | 5/2003 | Santini, Jr. et al. | |
| 2003/0102367 A1* | 6/2003 | Monette | G05B 19/4183 |
| | | | 235/376 |
| 2003/0105518 A1 | 6/2003 | Dutta | |
| 2003/0105530 A1 | 6/2003 | Pirhonen | |
| 2003/0171053 A1 | 9/2003 | Sanders | |
| 2003/0187495 A1 | 10/2003 | Cully et al. | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236563 A1 | 12/2003 | Fifer | |
| 2004/0093077 A1 | 5/2004 | White et al. | |
| 2004/0098095 A1 | 5/2004 | Burnside et al. | |
| 2004/0100415 A1* | 5/2004 | Veitch | B01L 3/545 |
| | | | 343/850 |
| 2004/0111149 A1 | 6/2004 | Stinson | |
| 2004/0127970 A1 | 7/2004 | Suanders et al. | |
| 2004/0143317 A1 | 7/2004 | Stinson et al. | |
| 2004/0167610 A1 | 8/2004 | Fleming, III | |
| 2004/0174261 A1* | 9/2004 | Volpi | G06K 7/0008 |
| | | | 340/572.1 |
| 2005/0000553 A1* | 1/2005 | Noguchi | A61B 1/00144 |
| | | | 134/84 |
| 2005/0003007 A1 | 1/2005 | Boix et al. | |
| 2005/0025667 A1* | 2/2005 | Christensen | A61L 2/0088 |
| | | | 422/33 |
| 2005/0148819 A1* | 7/2005 | Noguchi | A61B 1/00059 |
| | | | 600/133 |
| 2005/0149226 A1 | 7/2005 | Stevens et al. | |
| 2005/0159802 A1 | 7/2005 | Furst et al. | |
| 2005/0165317 A1 | 7/2005 | Turner et al. | |
| 2005/0194441 A1* | 9/2005 | Truong | A61L 2/186 |
| | | | 235/385 |
| 2005/0232964 A1* | 10/2005 | Fennimore, Jr. | A61F 2/954 |
| | | | 424/423 |
| 2005/0247319 A1 | 11/2005 | Berger | |
| 2006/0006999 A1 | 1/2006 | Walczyk et al. | |
| 2006/0017545 A1* | 1/2006 | Volpi | G01S 13/751 |
| | | | 340/10.4 |
| 2006/0109118 A1* | 5/2006 | Pelo | G06K 19/077 |
| | | | 340/572.1 |
| 2006/0119481 A1* | 6/2006 | Tethrake | A61B 50/10 |
| | | | 340/572.1 |
| 2006/0145840 A1* | 7/2006 | Klun | A61L 2/28 |
| | | | 340/539.22 |
| 2006/0145871 A1* | 7/2006 | Donati | B65D 23/00 |
| | | | 340/572.8 |
| 2006/0184224 A1* | 8/2006 | Angel | A61F 2/95 |
| | | | 623/1.11 |
| 2006/0244593 A1* | 11/2006 | Nycz | A61F 2/4425 |
| | | | 340/572.1 |
| 2007/0094303 A1* | 4/2007 | Zwingenberger | A61L 2/24 |
| 2007/0160494 A1* | 7/2007 | Sands | A61L 2/07 |
| | | | 422/26 |
| 2009/0035189 A1* | 2/2009 | Wu | A61L 2/20 |
| | | | 422/106 |
| 2009/0204250 A1* | 8/2009 | Potyrailo | G01D 9/005 |
| | | | 700/109 |
| 2010/0245055 A1* | 9/2010 | Freeman | A61L 2/081 |
| | | | 340/10.41 |
| 2012/0171075 A1* | 7/2012 | Burke | A61L 2/081 |
| | | | 422/22 |
| 2013/0057390 A1* | 3/2013 | Watt | G06K 19/0717 |
| | | | 340/10.1 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 04/023985 | 3/2004 |
| WO | WO 04/030571 | 4/2004 |
| WO | WO 05/048041 | 5/2005 |
| WO | WO 06/014666 | 2/2006 |

OTHER PUBLICATIONS

"Measurement software launched", Decision News Media, Apr. 28, 2004, downloaded from: http://web.archive.org/web/20051226182129/http://www.foodproductiondaily.com/news/., 2pgs.

"Next generation of RFID technology", Pro-Talk Ltd, Apr. 11, 2005, downloaded from: http://web.archive.org/web/20050414152859/http://www.processingtalk.com/news/ium/i., 2 pgs.

"Radio Frequency Identification (RFID)", Logistics and Materiel Readiness, Feb. 23, 2006, downloaded from: http://web.archive.org/web/20060322173331/http://www.acq.osd.mil/log/rfid/rfid_faq.htm., 8pgs.

"RFID Basics", ZIH Corp., downloaded from: http://web.archive.org/web/20051214001632/http://www.zebra.com/id/zebra/na/en/index/., 2 pgs., (2005).

"RFID technology moves to the next level", Pro-Talk Ltd, Apr. 7, 2005, downloaded from: http://web.archive.org/web20050414125423/http://www.electronicstalk. com/news/inr/inr , 2 pgs.

"RFID", Farlex, Inc., downloaded from: http://www.computing-dictionary.thefreedictionary.com/RFID, 2 pgs., (2014).

"RFID", Wikimedia Foundation, Inc,, downloaded from: http://web.archive.org/web/20060325233244/http://en.wikipedia.org/wiki/RFID, 10 pgs., (2006).

(56) References Cited

OTHER PUBLICATIONS

"Savi Sensor Tags™", Savi Technology Inc., downloaded from: http://web.archive.org/web/20061231204238/http://www.savi.com/products/pr.rfid.securi., 2 pgs., (2014).

"Savi Technology Releases New RFID Sensor Tags to Track and Monitor the Condition of Global Shipments", Savi Technology Inc., Nov. 28, 2005, downloaded from: http://www.prnewswire.com/news-releases/savi-technology-releases-new-rfid-sensor-tag., 3pgs.

"Securing the supply chain with 'Super RFID'", Pro-Talk Ltd, Aug. 19, 2005, downloaded from: http://web.archive.org/web/20070814121001/http://www.processingtalk.com/news/ium/i., 2 pgs.

"ShipDAS® Data-Logger", Scientific Solutions® Inc., downloaded from: http://labmaster.com/products/shipdas/html/shipdas_index.html, 6 pgs. (2014).

"Super RFID Gaining Momentum, But Still Years Off", RFID Update, Apr. 12, 2005, downloaded from: http://www.web.archive.org/web/20051222023306/http://www.rfidupdate.com/articles/index., 2pgs.

"Super RFID: UK company driving next-gneration development", Technology news, Apr. 6, 2006, downloaded from: http://web.archive org/web20050510080027/http://pda.physorg.com/news3621.html, 3 pgs.

"Super RFID" RFID news Jan. 25, 2005, downloaded from: http://web.archiveorg/web20050213014154/http://www.rfidnews.org/weblog/2005/01/2., 1 pg.

"Temperature Tracking", Smarten up your assets®, www.identecsolutions.com, 5 pgs (2002).

"UK team develops concept of sensory-perceptive RFID tags", Decision News Media SAS, Jun. 4, 2005, downloaded from: http://web.archive.org/web/20051102011146/http://www.nutraingredients.com/news/new., 2pgs.

"Welcome to the Sun RFID and Sensor Community!" Sun Microsystems, Inc., Jun. 5, 2006, downloaded from: http://web.archive.org/web/20060623004953/http://sun.java.net/rfid-sensors/, 2 pgs.

"Wireless revolutionises research with sensors", News from Instrumentel, Oct. 28, 2005, downloaded from http://web.archive.org/web/20060315012730/http://www.processingtalk.com/news/ium/i., 1 pg.

Active RFID Technology, SaviTag ST-602, 1 pg (1989).

Active RFID®,It makes sense, www.free2move.se, 2 pgs.

Anonymous, *Bioabsorbable stent mounted on a catheter having optical coherence tomography capabilities*, Research Disclosure, Sep. 2004, pp, 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Best, "2015: RFID is all over-make way for super RFID", CNET Networks, Jan. 25, 2005, downloaded from: http://web.archive org/web20051028180614/http://networks.silicon.com/lans/0,3902466., 3pgs.

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar. /Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathari et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

International Search Report for PCT/US2007/015883 filed Jul. 22, 2007, dated Dec. 19, 2007, 6 pgs.

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J Biomed. Mater. Res., vol. 70A, pp. 10-19 (2004).

Mauduit et al., *Hydrolytic degradation of films prepared from blends of high and low molecular weight poly(DL-lactic acid)s*, Biomed. Mater. Res., vol. 30 pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Caron. After. Dis., vol. 1(4), pp. 438-448 (Jul./Aug. 1990).

Nelson, "Colombian Logistics and Security Firm Deploys RFID-Based information Solution From Savi Technology to Continously Monitor Cargo Shipments", Savi Technology Inc., May 10, 2006, downloaded from: http://web.archive.org/web/20060708223039/http://www.savi.com/news/2006/2006.05.1., 3 pgs.

Nichols et al., *Electrical Insulation of Implantable Devices by Composite Polymer Coatings*, ISA Transactions, vol. 26(4), pp. 15-18 (1987).

Opasjumruskit et al.,"Self-Powered Wireless Temperature Sensors Exploit RFID Technology", IEEE Pervasive Computing, downloaded from: http://www.computer.org/csdl/mags/pc/2006/01/b1054-abs.html., Abstract only (2006).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

(56) References Cited

OTHER PUBLICATIONS

Tamai et al., *Initial and 6-Month Results of Biodegradable Poly-l-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials, vol. 16, pp. 441-445 (1995).
Yau et al., Modern Size-Exclusion Liquid Chromatography, Wiley-Interscience Publication, IX-XV (1979).

\* cited by examiner

RADIO FREQUENCY IDENTIFICATION MONITORING OF STENTS

CROSS-REFERENCE

This application is a divisional of U.S. application Ser. No. 14/609,184 filed Jan. 29, 2015 which is a continuation of U.S. application Ser. No. 12/796,546 filed Jun. 8, 2010 which is a divisional application of U.S. application Ser. No. 11/486,688, now U.S. Pat. No. 7,757,543, filed on Jul. 13, 2006, each of which are incorporated by reference herein.

BACKGROUND OF THE INVENTION

Field of the Invention

This invention relates to monitoring environmental exposure of stents using radiofrequency identification.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

A stent can be exposed to range of environmental conditions during manufacturing and storage, or generally, during the periodic of time between completion of manufacturing and implantation. The properties of polymeric stents or polymeric coatings on stents can be particularly sensitive to environmental conditions such as temperature, humidity, vibration, and shock. Exposure to extremes in such conditions can negatively affect, for example, mechanical properties and drug delivery.

SUMMARY

Certain embodiments of the present invention include a method of monitoring a stent comprising: method of monitoring a stent comprising: obtaining readings of an environmental parameter from a sensor adjacent to a stent, the sensor positioned within or on a container including the stent; and transmitting the readings from an RFID tag located within or on the container to a transceiver, wherein a maximum tolerance of the stent for the environmental parameter is stored on the RFID tag; and comparing the readings to the maximum tolerance for the environmental parameter.

Other embodiments of the present invention include a method of monitoring a stent comprising: method of monitoring a stent comprising: obtaining readings of an environmental parameter from a sensor adjacent to a stent, the sensor positioned within or on a container including the stent, wherein the readings are received by an RFID tag located within or on the container; and comparing the readings received by the RFID tag to a maximum tolerance for the environmental parameter.

DETAILED DESCRIPTION OF THE INVENTION

Various embodiments of the present invention relate to monitoring conditions of polymeric implantable medical devices, particularly stents, during manufacturing, storage, and transportation. The conditions of a stent can be monitored using Radio Frequency Identification (RFID) technology. RFID technology is known in the art. A significant advantage of the present invention is that it allows monitoring, storage, and analysis of the environmental exposure of a specific stent during all or part of the period of time between laser cutting to implantation.

The method and systems described herein may be may be applied in generally to implantable medical devices. The methods and systems are particularly relevant, for reasons discussed below, to implantable medical devices having a polymeric substrate, a polymer-based coating, and/or a drug-delivery coating. A polymer-based coating may contain, for example, an active agent or drug for local administration at a diseased site. An implantable medical device may include a polymer or non-polymer substrate with a polymer-based coating.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design. A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Figure 1:
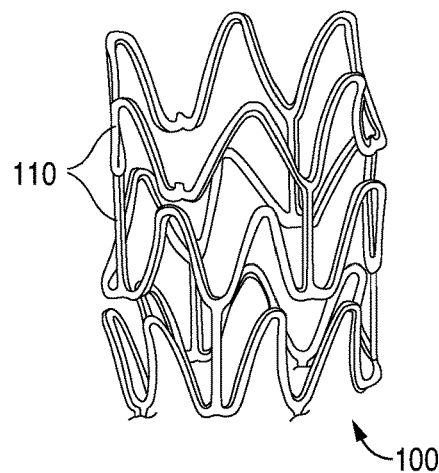
FIG. 1 depicts a stent.

The structure of a stent in particular can have a scaffolding or a substrate that includes a pattern of a plurality of interconnecting structural elements or struts. FIG. 1 depicts an example of a view of a stent 100. Stent 100 has a cylindrical shape and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In some applications the use of a femtosecond laser may be preferred. In other embodiments, chemical etching may be used to form a pattern on a tube.

A stent has certain mechanical requirements that are crucial to successful treatment. For example, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Bending elements 130, 140, and 150, in particular, are subjected to a great deal of stress and strain during use of a stent.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

However, the mechanical properties of polymers are particularly sensitive to changes in temperature. In particular, as the temperature increases, there is an increased susceptibility of polymer chains to move or rearrange which can negatively alter mechanical properties. Specifically, as the temperature approaches and surpasses the glass transition temperature, Tg, polymer chain rearrangement increases dramatically. Rearrangement of polymer chains is also time dependent. Thus, exposure of a polymer to a selected temperature and the amount of time a polymer is exposed to the selected temperature are important in assessing changes in polymer properties.

Tg is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

As the temperature of a polymer sample approaches Tg physical aging increases. Physical aging of a polymer refers to densification in the amorphous regions of a semicrystalline polymer. Densification is the increase in density of a material. Physical aging results in an increase in brittleness of a polymer which can result in cracking of struts upon crimping and deployment. Many polymers have Tg's low enough to allow significant physical aging or densification to occur during the time frame of storage, which can be a few days, a month, 3 months, 6 months, or more than 6 months. Even for polymers with Tg's above ambient temperatures, significant physical aging can occur during storage. Polymeric stents generally are stored below ambient temperatures to reduce or prevent physical aging.

Additionally, environmental conditions can also affect a drug coating on a stent. Temperature and humidity can influence the release rate of drug from a drug coating. If the environmental moisture or the temperature is high enough before the stent is implanted (e.g., during storage), much of the drug can be lost before implantation, changing the concentration of the drug resident on the stent. Drugs can also degrade at increased temperatures during manufacture and storage conditions, altering the total content and release rate of the drug. A drug may also be degraded during storage due to exposure to degradation agents present in the environment such as oxygen (air), light, or water (humidity, moisture).

Therefore, it would be advantageous to have available a system and method to monitor and record of the exposure of a stent to environmental conditions. The record could extend from the end stages of the manufacturing process, such as laser cutting, through implantation.

In some embodiments, a method of monitoring a device, such as a stent, may include obtaining environmental parameter readings from a sensor adjacent to a stent, the sensor positioned within or on a container including the stent. The readings may be transmitted from an RFID tag positioned in or on the container to an RFID transceiver. An RFID tag is typically an integrated circuit that can receive, transmit, or store data. The environmental parameters can include, but are not limited to, temperature, humidity, oxygen, light, vibration, and shock. Sensors for measuring these parameters are known in the art and are commercially available. For example, sensors for measuring temperature, humidity, vibration, and shock can be obtained from Savi Technology in Sunnyvale, Calif.

In certain embodiments, the RFID tag and the sensor are integrated. Instrumental Inc. of Leeds, England has developed a technology that has been named "Super RFID" which incorporates sensing using an RFID tag. Super RFID can be a sensor network or sensor telemetry. Sensor networks can be used to monitor conditions and record that data, and if necessary, set off an alert if a condition moves beyond a certain criteria.

Typically an RFID system includes a transceiver, scanning antenna, and RFID transponder or tag. The transceiver controls the antenna and collects data. The scanning antenna which transmits a Radio Frequency (RF) signal under control of the transceiver, receives an RF signal back from the RFID Transponder that is passed back to the transceiver. The RFID Transponder or RFID Tag contains the data that is being read and is normally located on or within a package containing a product to be monitored.

The scanning antenna transmits a Radio Frequency (RF) signal. The RF signal accomplishes two tasks: it provides a passive RFID tag with the energy to communicate and it provides a communication path between the RFID tag and the transceiver. When an RFID tag passes thru the electromagnetic field of the scanning antenna, it detects the presence of the RF signal and transmits the information contained in its microchip which in turn is picked up by the scanning antenna and the data is provided to the transceiver. If the RFID is a "passive" device, it also draws power from the magnetic field and uses this to power the circuits of the RFID tag.

There are three kinds of RFID tags: active, passive, and semi-passive. Active RFID tags have their own internal power source which is used to power any ICs that generate the outgoing signal. Many active tags have practical ranges of hundreds of meters, and a battery life of up to 10 years. Passive RFID tags have no internal power supply. The minute electrical current induced in the antenna by the incoming radio frequency signal provides just enough power for the integrated circuit (IC) in the tag to power up and transmit a response. Passive RFID tags are limited in the physical distance they can transmit their data. Semi-passive RFID tags are very similar to passive tags except for the addition of a small battery. This battery allows the tag IC to be constantly powered, which removes the need for the aerial to be designed to collect power from the incoming signal.

In some embodiments, a stent is packaged and stored in a container. The container may be designed to inhibit, prevent, or significantly minimize exposure of the stent to environmental conditions such as moisture, light, oxygen, etc. The stent may be packaged in the container before or after sterilization of the stent. A stent can be sterilized by radiation, such as electron beam (e-beam) or by a suitable sterilization fluid such as ethylene oxide.

Figure 2:
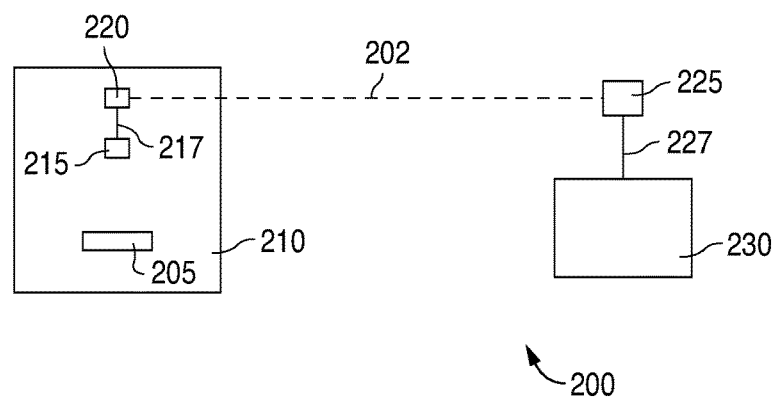
FIG. 2 depicts an exemplary RFID system for monitoring a stent in a container.

FIG. 2 depicts an exemplary RFID system 200 for monitoring a stent 205 in a sealed container 210. Container 210 can be provided for storage or packaging of a stent carrying a drug. Stents are typically sterilized, packaged, stored, and transported in a "ready to implant" configuration in which the stent is disposed at the distal end of a catheter. A stent can be crimped over a balloon. The stent-catheter system can be packaged prior to or after radiation sterilization. In one commercially distributed embodiment, container 210 also holds a balloon catheter assembly having stent 205 crimped onto a balloon.

Container 210 for a stent can be designed in any convenient form or shape that permits the effective enclosure of a stent or stent-catheter assembly contained therein. Container 210, however, should be compact and shaped so as to minimize storage space occupied by the container. For example, without limitation, container 210 can be in the shape of a tube, box or a pouch. In one commercially useful embodiment, container 210 can have a rectangular cross-section with a width between 8 in and 12 in and a length between 10 in and 13 in. Also, depending on the types of substance(s) used to construct container 210, container 210 can be of various degrees of rigidity or flexibility. Container 210 can be constructed of flexible films rather than rigid materials because it is less likely that the seal would be compromised by a change in atmospheric conditions during storage. For example, container 210 can be constructed of two sheets or lamina which have been joined along an edge. Also, container 210 can be constructed of a single sheet or lamina which has been folded and sealed along all edges or along all non-fold edges; or a bag or pocket which is sealed along one or more edges. The pouches can be made from a polymer, glass, ceramic, metallic substance, or a combination thereof. Typically, the pouches are made of metallic foil.

System 200 includes a sensor 215 configured to measure an environmental parameter. Sensor 215 can be coupled to container 210 either in or on container 210, depending upon the parameter to be measured. Sensor 215 can be coupled to container by, for example, gluing or taping. Sensor 215 can also be coupled to the stent, as described in U.S. Patent Appl. Pub. 2005016537.

Sensor 215 can measure the temperature, humidity, oxygen, light, vibration, or shock. To measure the exposure of a stent 205 to humidity or oxygen, sensor 215 should be placed within container 210. Container 210 can include any number of sensors corresponding to the number of environmental variables to be measured.

Container 210 can be stored individually from or stored together with other packaged stents. For example, container 210 can be disposed in a box, such as chipboard box, along with a number of similar or identical containers 210 including stents. The sensor and RFID tag in each container is configured to monitor exposure of a specific stent in the respective container.

Sensor 215 is configured to measure the temperature to which stent 205 is exposed. In general, a sensor 215 can be located close enough to stent 205 to obtain a reading of the temperature to which the stent is exposed. Specifically, sensor 215 can be positioned less than 0.5 mm, 1 mm, 2 mm, 5 mm, or 8 mm from stent 205.

As shown in FIG. 2, an RFID tag 220 is coupled to container 210. RFID tag 220 is configured to receive sensor data from sensor 215. RFID tag 220 can also transmit data to transceiver 225 which transmits the sensor data to storage and processing system 230. Sensor 215 and RFID tag 220 are communicatively coupled as shown by line 217. Sensor 215 and RFID tag 220 can communicate through, for example, a direct connection or wirelessly. Also, as indicated above, sensor 215 can be integrated with RFID tag 220.

RFID tag 220 is communicatively coupled with a transceiver 225 as shown by a line 202. RFID tag 220 can transmit data such as sensor data to transceiver 225. RFID tag 220 can transmit data to transceiver 225 wirelessly. Transceiver 225 can be incorporated into a form that is compact, such as a hand-device and can be disposed in any location within the range of RFID tag 220. For example, transceiver 225 can be located in a room where stents are stored, in a refrigerator or freezer where stents are stored, within a cargo container containing stents that are being shipped, or within a truck, airplane, or train. The range can depend upon whether RFID tag 220 is an active, passive, or semi-passive tag.

Transceiver 225 can transmit data it receives to storage and processing system 230, as shown by a line 227. System 230 can be any type of device capable of storing and/or processing data received from transceiver 225. For example, system 230 can be a desktop, laptop, mainframe, PDA, etc. Transceiver 225 can be located adjacent to or integrated into system 230. Alternatively, system 230 can be located in a remote location from transceiver 225. System 230 can be located at another location in the same city, in another state, or another country.

Maximum desired values or tolerances for monitored environmental parameters can be stored on, for example, RFID tag 220 or system 230. A condition, such as temperature, monitored by sensor 215 can be compared during specific times or at regular intervals to the tolerance value on RFID tag 220 or system 230. If the condition exceeds a tolerance for a parameter a signal can be automatically generated by RFID tag 220 or system 230. If the signal is generated by RFID tag 220, the signal can be transmitted to transceiver 225 for storage and processing on system 230. The signal can be automatically transmitted to transceiver 225 to alert potential users that a stent may or is defective. A flag can be stored on RFID tag 220 indicating that a tolerance has been exceeded. At any time subsequent to exposure to a tolerance level, a flag can be read from RFID 220 using transceiver 225.

Since the change in properties of a polymer are both time and temperature dependent, a time-temperature tolerance, a maximum time above a selected temperature, can also be stored. For example, a flag can be generated if a measured temperature exceeds a temperature that is a certain number of degrees below the Tg. If the time of exposure to a given temperature exceeds a time-temperature tolerance, a separate signal can be automatically generated by RFID tag 220 or system 230.

Sensor 215 can measure a parameter continuously over regularly spaced time intervals, such as seconds, minutes, days, etc. Sensor 215 can also be programmed to measure a parameter at specific points in time, in particular, during periods when extreme conditions can occur. For example, temperature measurements can be made during e-beam sterilization and shock and vibration measurements can be made during transport.

RFID tag 220 can be configured to store or transmit some or all of the measurements. Measurement data from RFID tag 220 can be transmitted continuously as measurements are made, over regularly spaced time intervals, or at particular points in time, such as in a manual scan of RFID tag 220 by transceiver 225. In one embodiment, a complete history of measurements of one or more environmental parameters can be stored on a database on RFID tag 220 or on system 230. In an embodiment, little or no measurement data is stored on RFID tag 220 or system 230. In this case, it may be desirable for RFID tag 220 to transmit data only when a maximum tolerance is exceeded.

In addition, numerous other types of data relating to stent 205 can be stored on RFID tag 220. Such data can include, but is not limited to, identification data, type of stent, date of manufacture, expiration date, and place of manufacture. Such information can be obtained either manually or automatically from RFID tag 220 using transceiver 225. In one useful embodiment, prior to an implant into a patient, a packaged stent can be scanned by a transceiver to determine whether the stent is defective and whether the stent is the correct stent for the implant procedure.

Additionally, information regarding various stents can be stored on system 230. This information can include expiration date and recall data. Upon scanning by a transceiver, such information can be compared to information relating to stent 205 stored on RFID tag 220. For example, identification data or date of manufacture can be used to determine if a stent is past its expiration date and should no longer be used. Also, the identification information of a stent can be used to determine if a stent has been recalled.

Sterilization is typically performed on medical devices, such as stents, cathethers, stent-catheter assemblies to reduce the bioburden on the device. Bioburden refers generally to the number of microorganisms with which an object is contaminated.

Radiation sterilization is well known to those of ordinary skill the art. Medical devices composed in whole or in part of polymers can be sterilized by various kinds of radiation, including, but not limited to, electron beam (e-beam), gamma ray, ultraviolet, infra-red, ion beam, x-ray, and laser. A sterilization dose can be determined by selecting a dose that provides a required reduction in bioburden.

However, it is known that radiation can alter the properties of the polymers being treated by the radiation such as e-beam radiation. High-energy radiation tends to produce ionization and excitation in polymer molecules. These energy-rich species undergo dissociation, abstraction, and addition reactions in a sequence leading to chemical stability. The stabilization process can occur during, immediately after, or even days, weeks, or months after irradiation which often results in physical and chemical cross-linking or chain scission. Resultant physical changes can include embrittlement, discoloration, odor generation, stiffening, and softening, among others.

As indicated above, polymer properties are particularly susceptible to changes in temperature. The rise in temperature is dependent on the level of exposure. A stent-catheter assembly can be exposed to e-beam radiation as high as 50 kGy during sterilization. As discussed above, increases in temperature of a polymeric stent can result in cracking of struts during deployment due to onset of brittle behavior. The increase in temperature can increase the release rate of drug resulting in a decrease of drug loading on a stent. Additionally, the deterioration of performance of polymeric materials and drugs due to e-beam radiation sterilization has been associated with free radical formation in a device during radiation exposure and by reaction with other parts of the polymer chains. The reaction is dependent on e-beam dose and level of temperature. Therefore, it is important to have knowledge of the temperature exposure of a stent before, during, and after a radiation sterilization process.

Figure 3:
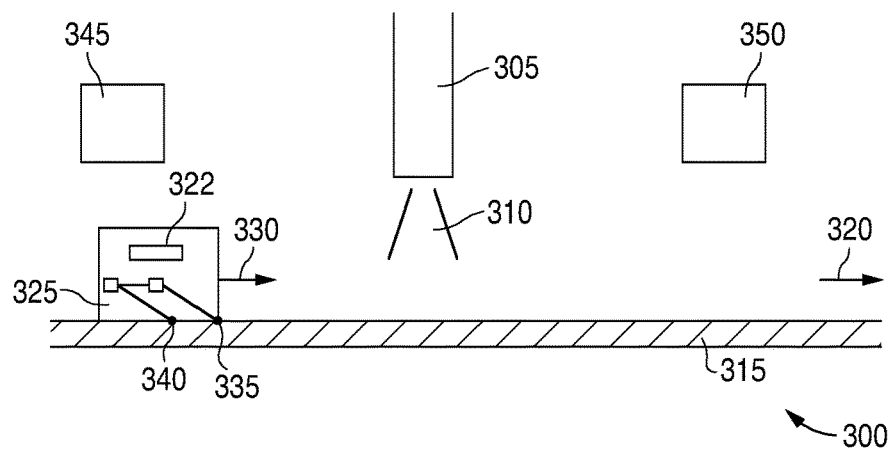
FIG. 3 depicts a schematic embodiment of an e-beam sterilization system.

FIG. 3 depicts a schematic embodiment of an e-beam sterilization system 300. System 300 includes an e-beam source 305 that emits an e-beam 310. A conveyer belt 315 moves as shown by an arrow 320. A stent 322 is disposed in a container 325 which is being moved by conveyer belt 315 as shown by an arrow 330.

Container 325 is moved through e-beam source 305 to expose stent 320 to e-beam 310. Container 325 has a temperature sensor 335 and an RFID tag 340 that is configured to receive temperature data from sensor 335. RFID tag 340 can transmit temperature data to transceiver 345 located before stent 320 passes through e-beam 310. Transceiver 345 can transmit the sensor data to a device (not shown) for storage or processing. Transceiver 345 can obtain temperature data from RFID tag 340 after stent 320 passes through e-beam 310. Transceivers can be configured to receive temperature data at any point along the conveyer. If the measured temperature exceeds a tolerance allowed during or after exposure to the e-beam, a signal can be generated by RFID tag 340, a transceiver, or a device communicating with a transceiver.

In some embodiments, container 325 with stent 322 can be cooled, e.g., in a refrigerator or freezer, prior to e-beam exposure. A transceiver can monitor the temperature of stent 322 during the cool down process prior to e-beam exposure to ensure the temperature of stent 322 is reduced sufficiently prior to e-beam exposure. The reduced temperature can be less than 10° C., 0° C., −15° C., −25° C., −40° C., −70° C., −100° C., −150° C., −200° C., −240° C., or less than −273° C. Thus, system 300 can provide documented assurance that every unit has been cooled down properly prior to sterilization.

A polymer for use in fabricating an implantable medical device, such as a stent, can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

While particular embodiments of the present invention have been shown and described, it will be obvious to those skilled in the art that changes and modifications can be made without departing from this invention in its broader aspects.

What is claimed is:
1. A system for monitoring a stent comprising:
an implantable medical device disposed within a sealed container, wherein the device comprises a bioabsorbable stent crimped over a delivery balloon, wherein the stent comprises a scaffolding including a network of interconnecting structural elements that comprise a polylactide-based polymer;
a sensor disposed within or on the sealed container capable of monitoring a temperature of exposure of the device, wherein the monitored temperature is compared to a temperature tolerance stored on the device and when the temperature tolerance is exceeded, an alert is generated.

2. The system of claim 1, wherein exceeding the temperature tolerance comprises exceeding a maximum temperature.

3. The system of claim 1, wherein exceeding the temperature tolerance comprises exceeding a time-temperature tolerance comprising a maximum time above a selected temperature.

4. The system of claim 1, wherein the container is disposed within a box and the container is a foil pouch.

5. The system of claim 1, wherein the sensor is integrated with an RFID tag which monitors conditions of exposure and records data.

6. The system of claim 1, wherein the sensor is positioned less than 8 mm from stent.

7. The system of claim 1, further comprising an RFID tag capable of storing and transmitting the monitored temperature.

8. The system of claim 7, wherein the RFID tag is configured to receive data from the sensor.

9. The system of claim 7, wherein the RFID tag is configured to transmit data to a transceiver which transmits data from the sensor to a storage and processing system.

10. The system of claim 7, wherein the sensor and RFID tag are communicatively coupled directly or wirelessly.

11. The system of claim 7, wherein the RFID tag is communicatively coupled with a transceiver and is configured to transmit data from the sensor to the transceiver directly or wirelessly.

12. The system of claim 11, wherein the transceiver is incorporated into a hand-device.

13. The system of claim 11, wherein the transceiver is at a location where stents are stored, the location selected from the group consisting of a refrigerator, freezer, within a cargo container, within a truck, within an airplane, and within a train.

14. The system of claim 11, wherein the transceiver is configured to transmit data it receives to a processing system.

15. The system of claim 14, wherein the processing system is selected from the group consisting of a desktop, laptop, mainframe, and PDA.

* * * * *